United States Patent
Gupta et al.

(10) Patent No.: US 6,852,759 B2
(45) Date of Patent: Feb. 8, 2005

(54) PROCESS FOR THE SYNTHESIS OF TRANS-ALKENOIC ACIDS, USE THEREOF

(75) Inventors: Vishwa Nath Gupta, Jammu (IN); Vikram Bhardwaj, Jammu (IN); Bhupinder Singh, Jammu (IN); Bal Krishan Chandan, Jammu (IN); Krishan Avtar Suri, Jammu (IN); Naresh Kumar Satti, Jammu (IN); Om Parkash Suri, Jammu (IN); Sukhdev Swami Handa, Jammu (IN)

(73) Assignee: Council of Scientific and Industrial Research, New Delhi (IN)

(*) Notice: Subject to any disclaimer, the term of this patent is extended or adjusted under 35 U.S.C. 154(b) by 0 days.

(21) Appl. No.: 10/113,220

(22) Filed: Mar. 28, 2002

(65) Prior Publication Data

US 2004/0024232 A1 Feb. 5, 2004

(51) Int. Cl.⁷ .......................... A01N 37/00; A61K 31/20
(52) U.S. Cl. ...................... 514/560; 514/557; 514/558; 554/223
(58) Field of Search .......................................... 581/223

(56) References Cited

PUBLICATIONS

JB Hale et al., JACS, 1930, 52:4536–4539.*
Huiying Wang et al., *Acta Botanica Yunnanica*, 1989, 11(1):60–64 with English abstract.
Mit Sumarn Tsujimoto, *J. Soc. Chem. Ind. Japan*, 1927, 30(12):868–873 with English abstract.
JB Hale et al., *J. Am. Chem. Soc.*, 1930, 52:4536–4539.
DG Bounds et al, *J. of Chem Soc.*, 1954, 448–451.
E. Klenk, *Chemical Abstract*, 1926, 21:54.
E. Klenk, *Chemical Abstract*, 1927, 21:2277.
J.B. Hale et al., *J. of American Chem. Soc.*, 1930, 52:4536–4539.
A. Müller et al., *Chemische Berichte*, 1939, 72:615–619.
J. March, "Advanced Organic Chemistry", 1985, 412–413.
Sharon Arrol et al., *Chem. Abstracts*, 2000, 150(2).
Christian Wolfrum et al., *Chem. Abstracts*, 2001, 98(5).
PCT search report.

\* cited by examiner

*Primary Examiner*—Deborah D. Carr
(74) *Attorney, Agent, or Firm*—Morgan & Finnegan, LLP

(57) ABSTRACT

The present invention relates to a process for the preparation of trans-alkenoic acids of general formula $CH_3-(CH_2)n-CH=(CH_2)mCO_2H$ where n=4 to 9 m=8 to 16. More particularly, the present invention relates to a process for the preparation of trans-tetracos-15-enoic acid, which is a bioactive constituent possessing dose-related hepatoprotective activity. The present invention also relates to the use thereof for hepatoprotection.

3 Claims, No Drawings

//PROCESS FOR THE SYNTHESIS OF TRANS-ALKENOIC ACIDS, USE THEREOF

FIELD OF THE INVENTION

The present invention relates to a process for he preparation of trans-alkenoic acids of general formula $CH_3$—$(CH_2)_n$—$CH=CH$—$(CH_2)_m CO_2 H$ where n=4 to 9 m=8 to 16 16. More particularly, the present invention relates to a process for the preparation of trans-tetracos-15-enoic acid, which is a bioactive constituent possessing dose-related hepatoprotective activity.

BACKGROUND OF THE INVENTION

Trans-alkenoic acids possess hepatoprotective activity comparable to/better than know formulations. Herbal preparations in use as antihepatotoxic/hepatoprotectives are non-standard both from biological and chemical aspects. The first report about natural occurrence of an acid of this type viz, trans-tetracos-15-enoic acid [Wang Huiying, Yu Xuetian, Yi Yuanfen & Ding Jingksi, *Yuman Zhiwu Yanjiu*, 1989, 11 (1), 60–4 (Ch)] as a constituent of Jojoba oil ex *Simmondsia chinensis* seeds (0.62–1.11%) was based on GLC analysis.

Both nervonic acid from the brain cerebrosides of cattle and man [Klenk, L. *Physiol Chem.* 1925, 145,244; 1926, 157, 283; 1927, 166, 268] and selacholeic acid from shark and ray-liver oils [Tsujimoto, *J. Soc. Chem. Ind., Japan* 1927, 30, 868] were formulated as cis-tetracos-15-enoic acids. The two identical natural products have been synthesized by malonate chain extension of cis-docos-13-enoic acid [J. B. Hale, W. H. Lycan and Roger Adams, *J. Am. Chem. Soc.*, 1930, 52, 4536; Muller & Benzer, *Ber.*, 1939, 72, 615]. In the process tetracos-15-enoic acid was prepared in six steps i.e., (a) Esterification of erucic yield (yield 93%). (b) Reduction of methylerucate with Na metal in n-butyl alcohol (yield 55%), (c) Conversion of erucyl alcohol to erucyl bromide by the action of $PBr_3$ (yield 50%) (d) Condensation of erucyl bromide with malonic ester over a period of forty eight hours (yield 78%). (e) Hydrolysis and decarboxylation of erucyl malonic ester to tetracos-15-enoic acid (yield 50%) (f) Isomerization of cis product to trans form (yield) 90%), in an overall yield of 9.05%.

D. G. Bounds, R. P. Linstead and B. C. L. Weedon, [*Journal of Chemical Society*, 1954, 448] report synthesis of cis and trans-tetracos-15-enoic acid by anodic chain extension of oleic and claidic acids respectively. This publication discloses the electrolysis of oleic and elaidic acids in presence of excess of methyl hydrogen substrate to give an expected mixture of three products by both symmetrical and unsymmetrical coupling of the two compounds. By distillation and hydrolysis of the unsymmetrical products, mixture of cis and trans-tetracos-15-enoic acids was obtained in 30–35% overall yield.

All the reported synthetic procedures for trans-alkenoic acids till date are lengthy, non-specific i.e., yielding mixture of cis and trans isomers and end up with very poor yields.

OBJECTS OF THE INVENTION

The main object of the present invention is to provide a synthetic method for the production of trans-alkenoic acids, hepatoprotective constituents of natural origin.

Another object is to report an economic high yielding synthesis, where the end product i.e., trans-alkenoic acids are obtained up to 70% in overall yield.

SUMMARY OF THE INVENTION

General formula of t-alkenoic acid has been described and when n=7 and m=13 it represents t-tetracos 15-enoic acid.

Accordingly the present invention provides a process for preparation of a trans-alkenoic acid of the formula $CH_3$—$(CH_2)_n$—$CH=CH$—$(CH_2)_m COOH$ wherein n is 4 to 9, m is 8 to 16, said process comprising (i) reducing a bis noralkenoic acid to the corresponding alkenol in the presence of metal hydride (ii) reacting the alkenol obtained above with a brominating agent at a temperature in the range of –10 to 25° C. for 1 to 4 hours and recovering the bromoalkene so formed, (iii) condensing the bromoalkene obtained above with dialkyl malonate, ethyl acetoacetate or ethyl cyanoacetate in he presence of an alkali metal alkoxide to give dicarbalkoyalkene followed by hydrolysis to give corresponding dicarboxylic acid, (iv) decarboxylating the dicarboxylic acid obtained above partially to trans-alkenoic acid.

In another embodiment of the invention the process relates to the preparation of trans-tetracos-15-enoic acid.

In yet another embodiment of the invention trans-tetracos-15-enoic acid shows dose-related hepatoprotective activity.

In yet another embodiment of the present invention the bis noralkenoic acid used is selected from the group consisting of trans-henicos-12-enoic acid, trans-docos-14-enoic acid, trans-icos-12-enoic acid, trans-tetradec-8-enoic acid and trans docos-13-enoic acid.

In a further embodiment of the invention, an organic acid is used in step (i), and said organic acid is selected from $Cl_3CCOOH$, $F_3CCOOH$ and the like.

In another embodiment of the invention, the metal hydride used in step (i) is selected from $LiAlH_4$, $NaBH_4$ and the like.

In another embodiment of the invention, the brominating agent used is selected from $PBr_3$ and $Ph_3P\text{-}Br_2$ complex.

In yet another embodiment the decarboxylation is carried out of heating the dicarboxylic acid in a dry stat or by heating in wet dimethyl sulphoxide containing NaCl, $Na_3PO_4$ or any other simple salt.

In yet another embodiment of the invention, the ether medium employed in step (i) is selected from diethyl either, tetrahydrofuran, dioxane and methyl cellosolve.

In another embodiment of the invention, the alkyl malonate used in step (iii) is selected from dimethylmalonate and diethylmalonate.

In another embodiment of the invention, the acetoacetate used in step (iii) is selected from ethyl acetoacetate and methyl acetoacetate.

In another embodiment of the invention the cyanoacetate used in step (iii) is selected from ethyl cyanoacetate and methyl cyanoacetate.

In another embodiment of the invention, the alkali metal alkoxide employed in (iii) is selected from Na/K methoxide and ethoxide.

In another embodiment of the invention, the hydrolysis of diester in step (iv) is carried out using aqueous or methanolic NaOH or KOH or $(CH_3)_3COK$ (1.5M–2.5M).

In another embodiment of the invention, the partial decarboxylation in step (v) is carried out by dry heating of the diacid at 170–200° C. in an oil bath or by heating in wet dimethyl sulphoxide containing NaCl, $Na_3PO_4$ or any other simply salt at 120–130° C.

In another embodiment of the invention, the solvent employed by crystallization of the product is selected from ethanol, ethanol, isopropanol and ethyl acetate.

The present invention also relates to the use of trans-alkenoic acids of general formula $CH_3$—$(CH_2)_n$—$CH=(CH_2)_m CO_2 H$ where n=4 to 9 m=8 to 16 for dose related hepatoprotection.

In another embodiment of the invention, the dose of trans-alkenoic acids of general formula $CH_3$—$(CH_2)_n$—$CH=CH$—$(CH_2)_m CO_2H$ where n=4 to 9 m=8 to 16 is in the range of 12.5 to 100 mg per kg body weight of the patient.

The present invention also relates to a method for hepatoprotection comprising administering to a patient a trans-alkenoic acid of general formula $CH_3$—$(CH_2)_n$—$CH=CH$—$(CH_2)_m CO_2H$ where n=4 to 9 m=8 to 16 in an amount of 12.5 to 100 mg per kg body weight of the patient.

The present invention also relates to a process for preparing a pharmaceutical composition for hepatoprotection comprising mixing a trans-alkenoic acid of general formula $CH_3$—$(CH_2)_n$—$CH=(CH_2)_m\ CO_2H$ where n=4 to 9 m=8 to 16 in a pharmaceutically acceptable carrier.

In one embodiment of the invention, the trans-alkenoic acid of general formula $CH_2$—$(CH_2)_n$—$CH=CH$—$(CH_2)_m CO_2H$ where n=4 to 9 m=8 to 16 is mixed in the pharmaceutically acceptable carrier to provide a dose of 12.5 to 100 mg per kg body weight of the patient.

DETAILED DESCRIPTION OF THE INVENTION

The present invention provides an improved high yielding process for the synthesis of trans-alkenoic acids particularly trans-tetracos-15-enoic acid, bioactive constituents possessing dose related hepatoprotective activity, which is based on malonate, acetoacetate or cyanoacetate chain extension of bis noralkenoic acids, comprising:

(i) Reduction of bis noralkenoic acids to corresponding alkenol using complex metal hydrides in the presence of catechol and/or an organic acid in ether medium.

(ii) Conversion of the alkenol to bromoalkene.

(iii) Condensation of the bromoene with dialkyl malonate or ethylacetoacetate or ethyl cyanoacetate in presence of alkali metal alkoxide.

(iv) Hydrolysis of 1,1-dicarbalkoxyalkene or 1-acetyl-1-carbalkoxyalkene or 1-cyano-1-carbalkoxyalkene to the corresponding dicarboxylic acid.

(v) Partial decarboxylation of the dicarboxylic acid to trans-alkenoic acid.

(vi) Crystallization of the final product from an organic solvent with 1–4 C atoms by chilling at subzero temperatures.

Complex metal hydride used in step (i) is preferably chosen from $LiAlH_4$, $NaBH_4$ or the like. Organic acid used in step (i) is preferably chosen from $Cl_3CCOOH$, $F_3CCOOH$ and the like. Ether medium employed in step (i) is preferably chosen from diethyl ether, tetrahydrofuran, dioxane or methyl cellosolve. Conversion of enol to bromocompound in step (ii) is preferably carried out with $PBr_3$ or $PH_3P$—$Br_2$ complex.

Alkyl malonate used in (iii) is preferably chosen from dimethylmalonate and diethylmalonate, acetoacetate is preferably chosen from ethyl acetoacetate or methyl acetoacetate and cyanoacetate is preferably chosen form ethyl cyanoacetate or methyl cyanoacetate. Alkali metal alkoxide employed in (iii) is preferably selected from Na/K methoxide and ethoxide.

Hydrolysis of diester in step (iv) is preferable carried out using aqueous or methanolic NaOH or KOH or $(CH_3)_3COK$ (1.5M–2.5M). Partial decarboxylation in step (v) is carried out by dry heating of the diacid at 170–200° C. in an oil bath or by heating in wet dimethyl sulphoxide containing NaCl, $Na_3PO_4$ or some other simple salt at 120–130° C. The solvent employed for crystallization of the final product is preferably chosen from methanol, ethanol, isopropanol or ethyl acetate.

The invention is described with reference to the examples given below which should not, however, be construed to limit the scope of present invention.

EXAMPLE 1 a. Reduction of docos-13-enoic acid to docos-13-enol

Lithium Aluminium Hydride (LAH, 6.9 g) was suspended in absolute diethyl ether in a three necked R.B. flask provided with a dropping funnel, a reflux condenser and a magnetic stirring paddle. To stirred suspension (placed in an ice bath), docos-13-enoic acid (50 g) dissolved in absolute diethyl ether (300 mL) was added dropwise, the operation being completed in one hour. The reaction mixture was further stirred for another half an hour at room temperature (22±3° C.). The reaction was quenched by adding ethyl acetate (100 mL) and 10% aq. $H_2SO_4$ (100 mL). Ether layer was separated, washed with water (5×50 mL) and dried over anhydrous $Na_2SO_4$. Ether was removed by distillation and reaction product recovered by vacuum distillation (200–203° C., 1 torr). Product (43 g, 90% yield) was characterized by $^1H$-NMR.

b. Conversion of docos-13-enol to bromodocos-13-ene

Docos-13-enol (50 g) was dissolved in dry toluene (160 g) and the solution was placed in a three necked R.B. flask fitted with a reflux condenser and a dropping funnel. The solution was cooled to −152 C. (cryostat) and $PBr_3$ (20 g) was added to it dropwise. After the addition, the reaction mixture was heated on a steam bath for four hours (Progress monitored on TLC). Toluene was removed from the reaction mixture by distillation and the residue was dissolved in n-hexane (200 mL), the solution was washed with aq. KOH (20%, 50 mL), aq. NaCl (10%, 50 mL), finally with water and then dried over anhydrous $MgSO_4$. Hexane was removed by distillation under atmospheric pressure and the product under diminished pressure (203–205° C. 1 torr), yield (55 g, 93%).

c. Conversion of bromodocos-13-ene to 1,1-dicarbalkoxytricos-14-ene

Absolute ethanol (15 mL) was taken in a three necked R.B. flask fitted with a dropping funnel and a reflux condenser. Sodium metal (600 mg) was added in ethanol, in small pieces, with constant stirring followed by dropwise addition of diethyl malonate (6 g) over fifteen minutes. This was followed by dropwise addition of bromoalkene (10 g). The reaction mixture was refluxed on a steam bath for four hours. Ethanol was removed from the reaction mixture on a rotavapour and to the residue HCl (1%, 100 mL) was added. The mixture was extracted with diethyl ether (5×100 mL). The ether extract was dried over anhydrous $Na_2SO_4$. Ether extract was concentrated to 50 ml, and then filtered through a small column (packed with neutral $Al_2O_3$) to get 1,1-dicarbalkoxytricos-14-ene, yield (11 g, 88%).

d. Hydrolysis of the 1,1-dicarbalkoxytricos-14-ene to 1,1-dicarboxytricos-14-ene Enediester (10 g) was suspended in 60% q. ethanolic KOH (6 g, 40 mL) and refluxed on a water bath for one hour. Ethanol was removed from the reaction mixture by distillation and the residual aqueous solution was acidified (pH= 3) with 10% aqueous $H_2SO_4$ and extracted with $CHCl_3$ (5×50 mL). $CHCl_3$ extract was dried over anhydrous $CaCl_2$ and then distilled. The residue on cooling gave 1,1-dicarboxytricos-14-ene, a solid mass, yield (8 g, 91%).

e. Thermal decomposition of the 1,1-dicarboxytricos-14-ene to t-tetracos-15-enoic acid Diacid (5.5 g) was taken in a R.B. flask (50 mL) and heated at 178° in a Woods metal bath for one hour. The product was recovered by distillation under reduced pressure and the distillate crystallized from methanol by chilling at −20° C., yield (3.92 g, m.p. 61° C., 80%).

EXAMPLE 2 a. Reduction of docos-13-enoic acid to docos-13-enol

To a suspension of $BaBH_4$ (0.76 g, 0.01 mole) in dry THF (20 mL), docos-13-enoic acid (3.38 g, 0.01 mole) in dry THP (20 mL) was added. $CF_3COOH$ (1.14 g, 0.01 mole) was added in 15 minutes at 0° C. and stirred for four hours at r.t. (22±3° C.). The reaction mixture was quenched with 3N-HCl (5 mL) and extracted with diethyl ether (3×10 mL). Ether extract was washed with 1N-aq. NaOH (2×5 mL), water (2×5 mL), brine (2×5 mL) and dried over anhydrous $MgSO_4$ Ether was removed by distillation and docos-13-enol recovered by vacuum distillation (200–203° C., 1 torr), yield (2.6 g, 81%).

b. Conversion of docos-13-enol to bromodocos-13-ene

To an ice-cold solution of enol (1.86 g), 5.76 m mole) and pyridine (0.72 g, 9.21 mmole) in $CH_3CN$ (12mL), solid $pH_3P\text{-}Br_2$ (3.16 g, 7.48 mmole) was added over 10 minutes. After stirring at r.t. (22±3° C.) for one hour (Progress monitored on TLC), the reaction mixture was washed with water (3×5 mL), dried over anhydrous $Na_2SO_4$ and distilled under diminished pressure (203–205° C., 1 torr), to get bromodocos-13-ene (2.18 g, 95%).

c. Conversion of bromodocos-13-ene to 1,1-dicarbalkoxytricos-14-ene

Absolute ethyl alcohol (7.5 mL) was taken in a three necked R.B. flask fitted with a dropping funnel and a reflux condenser. Cleaned Sodium metal (330 mg) was added in ethanol, in small pieces. When whole of the sodium metal was reacted, diethyl malonate (3 g) was added dropwise, with constant stirring over a period of 15 minutes. Following this bromodocos-13-ene (5 g) was added similarly. Reaction mixture was further stirred for four hours. The ethanol was completely removed from the reaction mixture and to the residue HCl (1%, 50 mL) was added. The mixture was extracted with diethyl ether (5×50 mL). The ether layer was dried over anhydrous $MgSO_4$. The ether extract was concentrated to 25 mL and then filtered through a small column (packed with neutral $Al_2O_3$) to get 1,1-dicarbalkoxytricos-14-ene, yield (5.4 g, 86%).

d. Hydrolysis of the 1,1-dicarbalkoxytricos-14-ene to 1,1-dicarboxytricos-14-ene The enediester (5 g) was suspended in 60% aq ethanolic potassium hydroxide (3 g, 20 mL) and refluxed on a water bath for 50 minutes. The ethyl alcohol was removed from the reaction mixture by distillation ad residual aqueous solution was acidified (pH=3–4) with 10% aqueous sulphuric acid and extracted with $CHCl_3$ (5×25 mL). The chloroform extract was dried over anhydrous $CaCl_2$ and then distilled. The residue on cooling gave 1,1-dicarboxytricos-14-ene, yield (3.9 g, 89%).

e. Thermal decomposition of the 1,1-dicarboxytricos-14-ene to t-tetracos-15-enoic acid The diacid (2.75 g) was taken in a R.B. flask (25 mL) and heated at 178° in a Woods metal bath for one hour. The product was recovered by distillation under reduced pressure and the distillate crystallized from methanol by chilling at −25° C. yield (19 g, m.p. 61° C., 79%).

EXAMPLE 3 a. Reduction of tetradec-8-enoic acid to tetradec-8-enol

To a suspension of $NaBH_4$ (0.3 g, 0.005 mole) in dry methyl cellosolve (15 mL), tetradec-8-enoic acid (1.13 g, 0.005 mole) in dry methyl cellosolve (15 mL) was added. $CF_3COOH$ (0.57 g, 0.005 mole) was added in 10 minutes at 0° C. and stirred for 3 hours at r.t. (22±3° C.). 2N-HCl (4.0 mL) was added to quench the reaction.

The quenched reaction mixture was extracted with diethyl ether (2×10 mL). Ether extract was washed with 1N-aq. NaOH (1×5 mL), water (1×5 mL), brine (1×5 mL) and dried over anhydrous $MgSO_4$. Ether was removed by distillation and product recovered by distillation under diminished pressure (180–185° C., 1 torr), to yield tetradec-8-enol (0.958, 93%).

b. Conversion of tetradec-8-enol to bromotetradec-8-ene

A mixture of the tetradec-8-enol (0.61 g), pyridine (0.36 g, 4.60 mmole) in $CH_3CN$ (8 mL) was cooled in an ice bath and solid $PH_3P\text{-}Br_2$ complex (1.60 g, 3.75 mmole) was added over 20 minutes. Reaction mixture was stirred at r.t. (22±32 C.) for two hours and washed with water (2×5 mL), dried over anhydrous $Na_2SO_4$ and subjected to vacuum distillation (178–180°, 1 torr), yield (0.72 g, 91%).

c. Condensation of bromotetradec-8-ene with dimethyl sodium malonate

Absolute methyl alcohol (10 mL), was placed in three necked R.B. flask fitted with dropping funnel and a reflux condenser. Sodium metal (450 mg) was added in methyl alcohol, in small pieces, accompanied by constant stirring. To clear solution of sodium methoxide, dimethyl malonate (4.2 g) was added dropwise over a period of ten minutes. After this bromotetradec-8-ene (6.5 g) was added in a similar manner. Reaction mixture was refluxed over a steam bath for two hours.

Methyl alcohol was distilled on a rotavapour and residue was treated with 70 mL of 1% aq. HCl. The mixture was extracted with diethyl ether (3×100 ml). Ether extract was dried over anhydrous $Na_2SO_4$ and concentrated to 50 mL and then filtered through a $SiO_2$ gel (50 g) column to get 1,1-dicarbalkoxypentadec-9-ene, yield (7.01 g, 91%).

d. Hydrolysis of the 1,1-dicarbalkoxypentadec-9-ene to 1,1-dicarboxypentadec-9-ene The enediester (10 g) was suspended in 60% aq. ethanolic KOH (6 g, 40 mL) and refluxed on a water bath for one hour. Ethanol was removed from the reaction mixture by distillation and the residual aqueous solution was acidified (pH=3) with 10% aqueous $H_2SO_4$ and extracted with $CHCl_3$ (5×50 mL). The $CHCl_3$ extract was dried over anhydrous $CaCl_2$ and then distilled. The residue on cooling gave 1,1-dicarboxypentadec-9-ene, yield (8 g, 91%)

e. Thermal decomposition of 1,1-dicarboxypentadec-9-ene to t-hexadecen-10-oic acid The diacid (5.5 g) was taken in a R.B. flask (50 mL) and heated at 178° in a Woods metal bath for one hour. The product was recovered by distillation under reduced pressure and the distillate crystallized from methanol by chilling at −20° C., yield (3.92 g, m.p. 61° C., 80%).

Pharmacological Activity t-Tetracos-15-enoic acid (TCA) has been evaluated for antihepatotoxicity/hepato-protective activity both on prophylactic and curative aspects in vivo using $CCl_4$, Paracetamol, Galactosamine and alcohol as hepatotoxins employing silymarin as positive standard. In almost all the aspects TCA has shown better protection and reversal of biochemical parameters better then those obtained with silymarin. The results of the pharmacological activity are given in Tables 1 to 9 below.

TABLE 1

Hexobarbitone sleep time and zoxazolamine paralysis time (in vivo) of trans-Tetracos-15 enoic acid (TCA) fed at 1 h before $CCl_4$ (50 μl. kg-1, p.o.) administration in mice

| Treatment | Dose mg kg$^{-1}$ p.o. | Hexobarbitone Sleeping time (min) | Hepatoprotection (%) | Zoxazolamine Paralysis time (min) | Hepatoprotection (%) |
|---|---|---|---|---|---|
| Vehicle Control | — | 23.33 ± 1.76 | — | 21.32 ± 1.36 | — |
| Vehicle + $CCl_4$ | — | 55.66 ± 1.87**b | — | 50.83 ± 3.10 | — |
| TCA Alone | 100 | 21.85 ± 1.34 | — | 19.94 ± 1.49 | — |
| TCA + $CCl_4$ | 12.5 | 44.16 ± 1.87*c | 35.55 ± 5.78 | 39.00 ± 1.93*c | 40.10 ± 6.55 |
| TCA + $CCl_4$ | 25 | 37.83 ± 2.31c | 55.14 ± 7.16 | 35.66 ± 3.28c | 51.40 ± 11.12 |
| TCA + $CCl_4$ | 50 | 31.66 ± 2.31c | 74.21 ± 6.27 | 30.00 ± 2.26c | 70.61 ± 7.68 |
| TCA + $CCl_4$ | 100 | 28.16 ± 2.30c | 85.04 ± 7.12 | 26.00 ± 1.93c | 84.17 ± 6.55 |
| Silymarin + $CCl_2$ | 50 | 36.33 ± 2.46c | 59.78 ± 7.60 | 34.66 ± 1.68c | 54.79 ± 5.72 | a Values represent the mean ± SE of six animals in each group.
H: Hepatoprotective activity was calculated as {1− (T − V/C −V)} × 100 where "T" is mean value of drug and $CCl_4$, "C" is mean value of $CCl_4$ alone and "V" is the mean value of vehicle treated animals.
b Difference in relation to vehicle treated control group.
c Difference in relation to $CCl_4$ control group.
P value "<0.05; **<0.01 (Dunnett's test).

TABLE 2

Hepatoprotective activity (in vivo) of trans-Tetracos-15 enoic acid (TCA) (prophylactic study) fed at 48$^{th}$, 2 h before and ≠h after $CCl_4$ (0.5 ml, Kg$^{-4}$, p.o.) induced hepatic injury in rats.

| Treatment | Dose mg/kg, p.o. | GPT (Units) | GOT (Units) | ALP$^b$ | Bilirubin (mg %) | Triglycerides (mg %) |
|---|---|---|---|---|---|---|
| Vehicle Control | — | 130.91 ± 17.33 | 138.12 ± 32.21 | 21.60 ± 2.16 | 0.13 ± 0.02 | 8.71 ± 1.06 |
| Vehicle + $CCl_4$ | — | 1604.01 ± 100.32 | 980.50 ± 37.95 | 53.13 ± 3.56 | 0.79 ± 0.03 | 15.23 ± 1.58 |
| TCA alone | 100 | 102.66 ± 28.41 | 110.53 ± 25.55 | 23.15 ± 2.92 | 0.17 ± 0.02 | 6.98 ± 0.79 |
| TCA + $CCL_4$ | 12.5 | 992.34 ± 73.25** (41.52 ± 4.97) | 695.16 ± 67.28** (33.87 ± 7.99) | 45.25 ± 2.37$^{NS}$ (26.32 ± 6.55) | 0.47 ± 0.01 (47.98 ± 2.02) | 13.51 ± 0.51$^{NS}$ (26.40 ± 7.84) |
| TCA + $CCl_4$ | 25 | 924.39 ± 39.82** (46.10 ± 2.70) | 674.44 ± 53.20** (36.33 ± 6.32) | 39.48 ± 2.46** (43.28 ± 7.81) | 0.42 ± 0.01** (55.33 ± 2.86) | 12.11 ± 0.70$^{NS}$ (47.72 ± 11.33) |
| TCA + $CCl_4$ | 50 | 636.69 ± 44.49** (65.66 ± 3.02) | 543.99 ± 79.93** (51.82 ± 9.94) | 35.19 ± 2.90** (56.81 ± 9.15) | 0.34 ± 0.01** (67.67 ± 2.30) | 11.89 ± 0.75$^{NS}$ (51.77 = 11.46) |
| TCA + $CCl_4$ | 100 | 419.72 ± 17.60** (80.39 ± 1.19) | 432.08 ± 37.38** (65.10 ± 4.50) | 30.14 ± 2.54** (72.92 ± 8.07) | 0.26 ± 0.02** (79.04 ± 3.57) | 11.20 ± 0.68$^{NS}$ (61.75 ± 1.44) |
| Silymarin + $CCl_4$ | 50 | 809.18 ± 45.35 (54.04 ± 2.99) | 543.60 ± 45.91 (50.68 ± 6.36) | 36.24 ± 1.77 (53.56 ± 5.65) | 0.40 ± 0.03 (59.09 ± 5.44) | 12.07 ± 0.97$^{NS}$ (48.46 ± 14.96) | a Values represent the mean ± SE and within parentheses hepatoprotective activity percent mean ± SE of six animals in each group.
H: Hepatoprotective activity was calculated as {1 − (T − V/C − V)} × 100 where "T" is mean value of drug and $CCl_4$, "C" is mean value of $CCl_4$ alone and "V" is the mean value of vehicle treated animals.
Unit: Each unit is μmole pyruvate/min/l.
b is μmole of p-nitrophenol formed/min/L,
P value *<0.05: **<0.01
$^{NS}$ > 0.05 (Dunnett's t 0 test).

TABLE 3

Hepatoprotective activity (in vivo) trans-Tetracos-15 enoic acid (TCA) (curative study) fed at 24$^{th}$, 48 h after $CCl_4$ (0.5 ml. Kg$^{-1}$, p.o.) induced hepatic injury in rats.

| Treatment | Dose mg/kg, p.o. | GPT (Units) | GOT (Units) | ALP$^b$ | Bilirubin (mg %) | Triglycerides (mg %) |
|---|---|---|---|---|---|---|
| Vehicle Control | — | 91.50 ± 12.53 | 97.22 ± 7.75 | 23.50 ± 2.58 | 0.12 ± 0.02 | 8.11 ± 0.65 |
| Vehicle + $CCl_4$ | — | 1512.97 ± 72.25 | 776.34 ± 80.51 | 65.07 ± 6.11 | 0.88 ± 0.06 | 14.08 ± 1.00 |
| TCA alone | 100 | 92.18 ± 15.75 | 82.13 ± 10.59 | 25.84 ± 2.32 | 0.16 ± 0.02 | 6.98 ± 0.86 |
| TCA + $CCl_4$ | 12.5 | 1001.86 ± 48.55** (35.59 ± 3.37) | 524.23 ± 34.93** (37.12 ± 5.14) | 51.81 ± 3.94$^{NS}$ (27.87 ± 9.48) | 0.54 ± 0.02** (44.52 ± 3.66) | 12.57 ± 0.61$^{NS}$ (24.12 ± 10.07) |
| TCA + $CCl_4$ | 25 | 772.68 ± 47.66** (51.52 ± 3.31) | 448.28 ± 54.88** (48.31 ± 8.808) | 50.92 ± 1.62* (34.03 ± 3.89) | 0.47 ± 0.03** (53.51 ± 4.06) | 11.81 ± 1.05$^{NS}$ (36.23 ± 18.23) |

TABLE 3-continued

Hepatoprotective activity (in vivo) trans-Tetracos-15 enoic acid (TCA) (curative study) fed at 24th, 48 h after $CCl_4$ (0.5 ml. $Kg^{-1}$, p.o.) induced hepatic injury in rats.

| Treatment | Dose mg/kg, p.o. | GPT (Units) | GOT (Units) | ALP[b] | Bilirubin (mg %) | Triglycerides (mg %) |
|---|---|---|---|---|---|---|
| TCA + $CCl_4$ | 50 | 582.12 ± 37.77** (64.76 ± 2.62) | 365.43 ± 29.43** (60.50 ± 4.33) | 43.63 ± 2.82** (51.57 ± 6.78) | 0.39 ± 0.02 (64.25 ± 3.76) | 11.06 ± 0.61* (48.86 ± 10.64) |
| TCA + $CCl_4$ | 100 | 457.55 ± 18.18** (73.41 ± 1.26) | 318.96 ± 16.15** (67.35 ± 2.38) | 32.93 ± 2.13 (77.31 ± 5.13) | 0.29 ± 0.02 (76.54 ± 3.66) | 10.37 ± 0.65** (61.02 ± 11.24) |
| Silymarin + $CCl_4$ | 50 | 677.55 ± 53.72** (58.16 ± 3.74) | 413.03 ± 24.98** (53.49 ± 3.67) | 48.44 ± 2.98** (39.99 ± 7.17) | 0.46 ± 0.03** (55.26 ± 4.05) | 11.40 ± 0.54[NS] (42.48 ± 8.75) |

[a]Values represent the mean ± SE and within parentheses hepatoprotective activity percent mean ± SE of six animals in each group.
H: Hepatoprotective activity was calculated as {1 − (T − V/C − V)} × 100 where "T" is mean value of drug and $CCl_4$, "C" is mean value of $CCl_4$ alone and "V" is the mean value of vehicle treated animals.
Unit: Each unit is μmole pyruvate/min/L.
[b]is μmole of p-nitrophenol formed/min/L,
P value *<0.05: **<0.01
[NS]>0.05 (Durrett's t 0 test).

TABLE 4

Hepatoprotective activity (in vivo) of trans-Tetracos-15 enoic acid (TCA) (prophylactic study) fed at 72 h, 48 h, 1 h Before inhalation of diethyl-ether and 1 h after acctaminophen (APAP) (200. Mg. $Kg^{-1}$ i.P., 6 h after exposure to diethyl-ether) in mice.

| Treatment | Dose Mg/kg, p.o. | GPT (Units) | GOT (Units) | ALP[b] | Triglycerides (mg %) |
|---|---|---|---|---|---|
| Vehicle Control | — | 179.47 ± 3085 | 129.74 ± 27.28 | 25.06 ± 2.65 | 8.76 ± 0.93 |
| Vehicle + APAP | — | 2775.87 ± 138.60 | 1407.19 ± 51.34 | 57.21 ± 2.24 | 17.07 ± 1.33 |
| TCA Alone | 100 | 146.00 ± 32.15 | 106.86 ± 30.15 | 27.15 ± 2.92 | 7.77 ± 0.56 |
| TCA + APAP | 12.5 | 2182.19 ± 137.86 (22.86 ± 5.31) | 1079.43 ± 98.66 (25.66 ± 7.72) | 50.41 ± 3.07 (21.27 ± 9.50) | 14.72 ± 0.68 (28.28 ± 8.27) |
| TCA + APAP | 25 | 1696.53 ± 48.31 (41.57 ± 1.86) | 880.10 ± 60.29 (41.26 ± 4.72) | 46.23 ± 1.73 (34.15 ± 5.39) | 13.47 ± 0.89 (43.32 ± 10.80) |
| TCA + APAP | 50 | 1066.99 ± 118.14 (65.82 ± 4.55) | 619.36 ± 88.89 (61.67 ± 6.96) | 41.44 ± 1.27 (49.04 ± 3.94) | 12.34 ± 0.85 (56.84 ± 10.23) |
| TCA + APAP | 100 | 539.60 ± 51.65 (86.13 ± 1.99) | 310.53 ± 45.32 (85.85 ± 4.25) | 35.08 ± 2.18 (68.82 ± 6.78) | 10.87 ± 0.69 (74.48 ± 8.37) |
| Silymarin + APAP | 50 | 1060.09 ± 88.87 (65.97 ± 3.44) | 716.83 ± 44.44 (53.52 ± 2.17) | 42.53 ± 1.90 (45.66 ± 5.93) | 12.48 ± 0.86 (55.27 ± 10.39) |

[a]Values represent the mean ± SE and within parentheses hepatoprotective activity percent mean ± SE of six animals in each group.
H: Hepatoprotective activity was calculated as {1 − (T − V/C − V)} × 100 where "T" is mean value of drug and "APAP"
"C" is mean value of APAP alone and "V" is the mean value of vehicle treated animals.
Unit: Each unit is μmole pyruvate/min/L.
[b]is μmole of p-nitrophenel formed/min/L,
P value *<0.05: **<0.01
[NS]>0.05 (Dunnett's t 0 test).

TABLE 5

Hepatoprotective activity (in vivo) trans- Tetracos-15 enoic acid (TCA) (curative study) fed at 1 h, 24 h, 48 h, 72 h after acetaminophen (APAI*) (200. mg $kg^{-1}$ I.p. 6 h after exposure to diethyl-ether) in mice

| Treatment | Dose Mg/kg p.o. | GPT (Units) | GOT (Units) | ALP[b] | Triglycerides (mg %) |
|---|---|---|---|---|---|
| Vehicle Control | — | 145.94 ± 21.48 | 129.74 ± 27.28 | 25.06 ± 2.65 | 8.76 ± 0.93 |
| Vehicle + APAP | — | 682.11 ± 83.73 | 1407.19 ± 51.34 | 57.21 ± 2.24 | 17.07 ± 1.33 |
| TCA Alone | 100 | 129.65 ± 24.84 | 133.77 ± 20.84 | 22.57 ± 2.95 | 7.43 ± 0.89 |
| TCA + APAP | 12.5 | 431.85 ± 25.52** (49.67 ± 2.81) | 1079.43 ± 98.66[NS] (25.66 ± 7.72) | 50.41 ± 3.07[NS] (21.27 ± 9.50) | 14.72 ± 0.68[NS] (28.28 ± 8.27) |

TABLE 5-continued

Hepatoprotective activity (in vivo) trans- Tetracos-15 enoic acid (TCA) (curative study)
fed at 1 h, 24 h, 48 h, 72 h after acetaminophen (APAI*) (200. mg kg$^{-1}$ I.p.
6 h after exposure to diethyl-ether) in mice

| Treatment | Dose Mg/kg p.o. | GPT (Units) | GOT (Units) | ALP$^b$ | Triglycerides (mg %) |
|---|---|---|---|---|---|
| TCA + APAP | 25 | 320.07 ± 41.33** (67.52 ± 7.71) | 880.10 ± 60.29* (41.26 ± 4.72) | 46.23 ± 1.73* (34.15 ± 5.39) | 13.47 ± 0.89$^{NS}$ (43.32 ± 10.80) |
| TCA + APAP | 50 | 282.74 ± 32.96** (74.48 ± 6154.55) | 619.36 ± 88.89** (61.67 ± 6.96) | 41.44 ± 1.27** (49.04 ± 3.94) | 12.34 ± 0.85** (56.84 ± 10.23) |
| TCA + APAP | 100 | 235.59 ± 22.77** (83.33 ± 1.99) | 310.53 ± 45.32** (85.85 ± 4.25) | 35.08 ± 2.18** (68.82 ± 6.78) | 10.87 ± 0.69** (74.48 ± 8.37) |
| Silymarin + APAP | 50 | 1060.09 ± 88.87** (65.97 ± 3.44) | 348.64 ± 344.76** (55.22 ± 8.39) | 42.53 ± 1.90 (45.66 ± 5.93) | 12.48 ± 0.86 (55.27 ± 10.39) |

$^a$Values represent the mean ± SE and within parentheses hepatoprotective activity percent mean ± SE of six animals in each group.
H: Hepatoprotective activity was calculated as $\{1 - (T - V/C - V)\} \times 100$ where "T" is mean value of drug and "APAP"
"C" is mean value of APAP alone and "V" is the mean value of vehicle treated animals.
Unit: Each unit is μmole pyruvate/min/L.
$^b$is μmole of p-nitrophenol formed/min/L,
P value *<0.05; **<0.01
$^{NS}$>0.05 (Dunnett's t 0 test).

TABLE 6

Hepatoprotective activity (in vivo) of trans- Tetracos-15 enoic acid (TCA) (prophylactic study)
fed at 72 h, 48 h, 24 h, Before and 6 h after D-Galactosamine (Gal N)
300. Mg. Kg$^{-1}$ . s.c.) induced hepatic injury in rats

| Treatment | Dose Mg kg$^{-1}$, p.o. | GPT (Units) | GOT (Units) | Bilirubin (mg %) | ALP$^b$ | Triglycerides (mg %) |
|---|---|---|---|---|---|---|
| Vehicle Control | — | 97.98 ± 9.97 | 116.94 ± 20.76 | 0.17 ± 0.02 | 22.92 ± 1.89 | 7.48 ± 0.85 |
| Vehicle Gal N | — | 1161.74 ± 54.83 | 859.24 ± 60.38 | 0.82 ± 0.03 | 59.26 ± 2.63 | 32.84 ± 2.58 |
| TCA Alone | 100 | 95.22 ± 8.74 | 122.47 ± 11.84 | 0.20 ± 0.02 | 19.84 ± 1.58 | 8.79 ± 0.55 |
| TCA + Gal N | 12.5 | 743.62 ± 66.83** (39.30 ± 6.25) | 613.20 ± 65.19** (34.60 ± 7.57) | 0.56 ± 0.03** (39.49 ± 4.59) | 47.07 ± 2.98** (30.88 ± 7.77) | 26.49 ± 1.88* (37.38 ± 6.18) |
| TCA + Gal N | 25 | 635.11 ± 54.67** (49.35 ± 5.16) | 505.26 ± 29.63** (47.68 ± 3.99) | 0.44 ± 0.05** (58.00 ± 3.86) | 40.49 ± 2.29** (51.62 ± 6.31) | 23.58 ± 2.02 (46.97 ± 6.67) |
| TCA + Gal N | 50 | 413.53 ± 23.94** (70.34 ± 2.25) | 406.05 ± 25.82** (61.05 ± 3.48) | 0.36 ± 0.02** (70.76 ± 2.78) | 34.94 ± 1.43** (66.91 ± 3.92) | 21.37 ± 1.51** (54.25 ± 4.97) |
| Silymarin + Gal N | 50 | 587.98 ± 54.95** (53.94 ± 5.13) | 458.13 ± 40.69** (54.03 ± 5.48) | 0.44 ± 0.02 (58.71 ± 4.13) | 42.08 ± 2.56** (47.25 ± 7.05) | 28.85 ± 1.85 (29.61 ± 6.08) |

$^a$Values represent the mean ± SE and within parentheses hepatoprotective activity percent mean ± SE of six animals in each group.
H: Hepatoprotective activity was calculated as $\{1 - (T - V/C - V)\} \times 100$ where "T" is mean value of drug and "GalN"
"C" is mean value of GalN alone and "V" is the mean value of vehicle treated animals.
Unit: Each unit is μmole pyruvate/min/L.
$^b$is μmole of p-nitrophenol formed/min/L,
P value *<0.05; **<0.01
$^{NS}$>0.05 (Dunnett's t 0 test).

TABLE 7

Hepatoprotective activity (in vivo) trans- Tetracos-15 enoic acid (TCA) (curative study)
fed at 6 h, 24 h, 48 h And 72 h after D-Galactosamine (Gal N)
(300. Mg. Kg$^{-1}$ . s.c.) induced hepatic injury in rats"

| Treatment | Dose Mg/kg, p.o. | GPT (Units) | GOT (Units) | Bilirubin (mg %) | ALP$^b$ | Triglycerides (mg %) |
|---|---|---|---|---|---|---|
| Vehicle Control | — | 95.23 ± 7.82 | 87.37 ± 6.88 | 0.15 ± 0.02 | 26.99 ± 2.53 | 5.79 ± 0.93 |
| Vehicle Gal N | — | 905.48 ± 58.27 | 705.43 ± 49.39 | 0.92 ± 0.03 | 60.78 ± 3.72 | 14.81 ± 2.54 |
| TCA Alone | 50 | 105.02 ± 18.74 | 91.07 ± 10.50 | 0.19 ± 0.02 | 24.45 ± 2.76 | 6.44 ± 0.38 |
| TCA + Gal N | 12.5 | 578.14 ± 57.37** (40.40 ± 7.08) | 494.53 ± 41.13** (34.12 ± 6.65) | 0.56 ± 0.03** (46.75 ± 3.74) | 46.03 ± 2.35$^{NS}$ (43.65 ± 6.96) | 11.85 ± 0.75$^{NS}$ (32.78 ± 8.37) |

TABLE 7-continued

Hepatoprotective activity (in vivo) trans- Tetracos-15 enoic acid (TCA) (curative study) fed at 6 h, 24 h, 48 h And 72 h after D-Galactosamine (Gal N) (300. Mg. Kg$^{-1}$ . s.c.) induced hepatic injury in rats"

| Treatment | Dose Mg/kg, p.o. | GPT (Units) | GOT (Units) | Bilirubin (mg %) | ALP[b] | Triglycerides (mg %) |
|---|---|---|---|---|---|---|
| TCA + Gal N | 25 | 518.66 ± 42.64** (47.74 ± 5.26) | 449.93 ± 31.58** (41.37 ± 5.10) | 0.46 ± 0.03** (59.74 ± 4.04) | 38.87 ± 2.62** (64.83 ± 7.74) | 10.48 ± 0.91[NS] (46.11 ± 9.77) |
| TCA + Gal N | 50 | 412.17 ± 31.17** (60.88 ± 3.85) | 391.66 ± 29.53** (50.76 ± 4.78) | 0.35 ± 0.02 (73.16 ± 2.95) | 36.94 ± 1.87** (71.88 ± 5.54) | 9.23 ± 0.59* (61.84 ± 6.59) |
| Silymarin + Gal N | 50 | 475.43 ± 53.47** (53.07 ± 6.60) | 393.83 ± 26.42** (50.41 ± 4.27) | 0.45 ± 0.03** (60.17 ± 4.17) | 45.24 ± 3.01[NS] (45.99 ± 8.91) | 12.39 ± 1.58[NS] (26.75 ± 17.58) |

[a]Values represent the mean ± SE and within parentheses hepatoprotective activity percent mean ± SE of six animals in each group.
H: Hepatoprotective activity was calculated as $\{1 - (T - V/C - V)\} \times 100$ where "T" is mean value of drug and "GalN" "C" is mean value of GalN alone and "V" is the mean value of vehicle treated animals.
Unit: Each unit is μmole pyruvate/min/L.
[b]is μmole of p-niotrophenol formed/min/L,
P value *<0.05: **<0.01
[NS]>0.05 (Dunnett's t 0 test).

TABLE 8

Hepatoprotective activity (in vivo) trans-Tetracos-15 enoic acid (TCA) against alcohol induced damage charge in rats"

| Serum Parameters | Units | Gr. I Vehicles control | Gr. II Vehicle + Alcohol | Gr. III TCA (25 mg. Kg$^{-1}$) + Alcohol | Gr. IV TCA (50 mg. Kg$^{-1}$) + Alcohol | Gr. V Silymarin (50 mg. Kg$^{-1}$) + Alcohol |
|---|---|---|---|---|---|---|
| SGOT | U/l | 296.00 ± 9.79 | 357.00 ± 33.39 | 310.00 ± 30.36β | 295.00 ± 34.39β | 353.00 ± 29.71**β |
| % Protection | — | — | — | 77.29 | 101.09 | 39.43 |
| SGPT | U/l | 199.00 ± 16.34 | 281.00 ± 12.39 | 234.00 ± 8.80β | 220.00 = 11.30β | 224.00 ± 11.76**β |
| % Protection | — | — | — | 57.33 | 73.86 | 49.03 |
| GGT | IU/l[b] | 1.42 ± 0.303 | 2.69 ± 0.701 | 1.90 ± 0.447 | 1.54 ± 0.128 | 1.43 ± 0.157 |
| % Protection | — | — | — | 63.00 | 90.00 | 100.00 |
| ALF | U/l[b] | 14.00 ± 1.23 | 24.00 ± 1.60 | 16.00 ± 2.04 | 14.60 ± 2.82*β | 13.80 ± 2.016β |
| % Protection | — | — | — | 80.00 | 95.00 | 100.00 |
| Protein | G/dl | 11.70 ± 3.14 | 10.50 ± 2.10 | 16.90 ± 3.38 | 12.60 ± 3.09 | 10.80 ± 3.26 |
| % Protection | — | — | −10.30 | 44.40 | 7.70 | −7.70 |

[a]Values represent the mean ± SE of six animals in each group.
H: Hepatoprotective activity was calculated as $\{1 - (T - V/C - V)\} \times 100$ where "T" is mean value of drug and Alcohol "C" is mean value of Alcohol alone and "V" is the mean value of vehicle treated aninmals.
[1]Each unit is μmole pyruvate/min/L.
[2]is μmole p-nitrophenol formed/min,
[b]is μmole p-nitrophenol formed/min/L,
P value *<0.05; <0.01 *<0.001 (Student's t-test; and others are not significant.

TABLE 9

Hepatoprotective activity (in vivo) trans-Tetracos-15 enoic acid (TCA) against alcohol induced hepatic damage in rats"

| Hepatic Parameters | Units | Gr. I Vehicle control | Gr. II Vehicle + Alcohol | Gr. III TCA (25 mg. Kg$^{-1}$) + Alcohol | Gr. IV TCA (50 mg. Kg$^{-1}$) + Alcohol | Gr. V Silymarin (50 mg. Kg$^{-1}$) + Alcohol |
|---|---|---|---|---|---|---|
| SDII | Units/G[3] | 9.13 ± 0.196 | 7.58 ± 0.338**β | 7.79 ± 0.272 | 8.24 ± 0.390 | 8.18 ± 0.133*β |
| % Protection | — | — | 14 | 43 | 39 |
| G-6-Pase | Units/g[4] | 2.36 ± 0.235 | 1.73 ± 0.135 | 2.19 ± 0.465 | 2.20 ± 2.223 | 2.20 ± 0.356 |
| % Protection | — | — | 73 | 75 | 75 |
| Protein | Mg/g | 179.0 ± 8.23 | 168 ± 7.51 | 172 ± 20.430 | 174 ± 2.11 | 181 ± 6.89 |
| % change[5] | — | −7.1 | −3.9 | −2.80 | 1.1 |

TABLE 9-continued

Hepatoprotective activity (in vivo) trans-Tetracos-15 enoic acid (TCA) against alcohol induced hepatic damage in rats"

| Hepatic Parameters | Units | Gr. I Vehicle control | Gr. II Vehicle + Alcohol | Gr. III TCA (25 mg. Kg$^{-1}$) + Alcohol | Gr. IV TCA (50 mg. Kg$^{-1}$) + Alcohol | Gr. V Silymarin (50 mg. Kg$^{-1}$) + Alcohol |
|---|---|---|---|---|---|---|
| TG | Mg/g | 15.22 ± 4.874 | 16.56 ± 1.496 | 14.75 ± 0.60 | 15.44 ± 1.073 | 14.67 ± 2.589 |
|  | % change | — | 8.8 | −3.10 | 1.40 | −3.6 |

[a]Values represent the mean ± SE of six animals in each group.
H: Hepatoprotective activity was calculated as $\{1 - (T - V/C - V)\} \times 100$ where "T" is mean value of drug and Alcohol
"C" is mean value of Alcohol alone and "V" is the mean value of vehicle treated animals.
[2]is µmole K$_3$ Fe(CN)$_6$, utilised/min,
[4]is µmole of phosphate formed/min,
[5]Represent only change and not protection.
P value *<0.05; <0.01 *<0.001 (Student's t-test) and others are not significant.

Advantages of the Invention a) The number of steps have been reduced, one such step being direct reduction of acid to alcohol without using esterification route.
b) Use of modified reagents viz, Ph$_3$P-Br$_2$ in place of PBr$_3$ has resulted in higher yields.
c) Reaction time has been appreciably reduced even in malonate condensation and hydrolysis steps.
d) The product obtained is mainly the desired trans isomer, believed to be due to thermodynamic control.
e) The procedure can be effectively and economically employed for the synthesis of trans-alkenoic acids from corresponding bis-noralkenoic acids.

What is claimed is:

1. A method for of providing hepatoprotection comprising administering to a patient a trans-alkenoic acid of general formula CH3—(CH2)n—CH=CH—(CH2)m—CO2H where n=4 to 9, m=8 to 16 in an amount of 12.5 to 100 mg per kg body weight of the patient.

2. A process for preparing a pharmaceutical composition for hepatoprotection comprising mixing a trans-alkenoic acid of general formula CH3—(CH2)n—CH=CH—(CH2)m—CO2H where n 4 to 9, m=8 to 16 in a pharmaceutically acceptable carrier.

3. A process as claimed in claim 2 wherein the trans-alkenoic acid of general formula CH3—(CH2)n—CH=CH—(CH2)m—CO2H where n=4 to 9, m=8 to 16 is mixed in the pharmaceutically acceptable carrier to provide a dose of 12.5 to 100 mg per kg body weight of the patient.

* * * * *